(12) United States Patent
Miller et al.

(10) Patent No.: US 6,916,446 B1
(45) Date of Patent: Jul. 12, 2005

(54) BIOREACTOR METHOD, APPARATUS AND PRODUCT THEREBY

(75) Inventors: Laurence G. Miller, El Granada, CA (US); Ronald S. Oremland, Brisbane, CA (US); Shaun M. Baesman, San Mateo, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 167 days.

(21) Appl. No.: 10/251,697

(22) Filed: Sep. 18, 2002

(51) Int. Cl.⁷ .......................... A61L 9/00; A61L 12/10; B01D 15/08; C12P 1/04; G01D 21/02

(52) U.S. Cl. .................. 422/28; 422/1; 422/5; 422/32; 422/37; 422/119; 422/261; 422/305; 435/41; 435/132; 435/170; 435/183; 435/262.5

(58) Field of Search ................ 435/41, 132, 170, 435/183, 262.5; 422/1, 5, 28, 32, 37, 119, 261, 305

(56) References Cited

U.S. PATENT DOCUMENTS

| | | | |
|---|---|---|---|
| 4,266,034 A | 5/1981 | Patel et al. ................ | 435/253 |
| 4,269,940 A | 5/1981 | Patel et al. ................ | 435/148 |
| 4,492,756 A | 1/1985 | Ghisalba et al. ........... | 435/253 |
| 4,971,698 A | 11/1990 | Weber et al. .............. | 210/615 |
| 5,037,551 A | 8/1991 | Barkley et al. ............ | 210/603 |
| 5,057,221 A | 10/1991 | Bryant et al. .............. | 210/610 |
| 5,116,506 A | 5/1992 | Williamson et al. ........ | 210/610 |
| 5,958,757 A | 9/1999 | Steffan et al. ............ | 435/262.5 |
| 6,013,254 A | 1/2000 | Oremland et al. ......... | 424/93.4 |
| 6,051,198 A | 4/2000 | Sano et al. .............. | 423/240 S |
| 6,218,172 B1 | 4/2001 | Koziollek et al. ........ | 435/262.5 |
| 2003/0147773 A1 * | 8/2003 | Bryner et al. ................ | 422/28 |

OTHER PUBLICATIONS

Osol, A. et al. (eds.). Remington's Pharmaceutical Sciences.1980. 16th Edition. Philadelphia College of Pharmacy and Science. p. 1506.*
Article: "Large carbon isotope fractionation associated with oxidation of methyl halides by methylotrophic bacteria". Miller et al., PNAS, May 8, 2001, vol. 98, No. 10, pp. 5833–5837.
Article: "Consumption of Tropospheric Levels of Methyl Bromide by C1 Compound–Utilizing Bacteria and Comparison to Saturation Kinetics", Goodwin et al., Applied and Environmental Microbiology, Dec. 2001, pp. 5437–5443.
Article: "Bacterial Oxidation of Methyl Bromide in Mono Lake. California" Connell et al., Environ. Sci. Technol., 1997. 31, pp. 1489–1495.
Article: "Oxidation of Methyl Halides by Facultative Methylotroph Strain IMB–1". Schaefer et al., Applied and Environmental Microbiology, Nov. 1999. pp. 5035–5041.
Article: "Methyl bromide adsorption on activated carbon to control emissions from commodity fumigations", Leesch et al., Journal of Stored Products Research 36 (2000), pp. 65–74.
Article: "Methyl Bromide Recovery on Activated Carbon with Repeated Adsorption and Electrothermal Regeneration", Snyder et al., Ind. Eng. Chem. Res., 2001, 40, pp. 2925–2933.

* cited by examiner

Primary Examiner—Ralph Gitomer
Assistant Examiner—Kailash C. Srivastava
(74) Attorney, Agent, or Firm—Mark Homer

(57) ABSTRACT

Methyl halide contaminants are oxidized in a reaction chamber containing a methylotrophic bacterium through direct oxidation of the methyl halide contaminant. Methyl halides may be used as a disinfectant, with the remnant methyl halide contaminant oxidized through direct oxidation by the methylotrophic bacterium.

15 Claims, 9 Drawing Sheets

US 6,916,446 B1

BIOREACTOR METHOD, APPARATUS AND PRODUCT THEREBY

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention relates to direct oxidation of methyl halides by a methylotrophic bacterium in a bioreactor.

2. Brief Description of the Related Art

Use of methyl bromide (MeBr) as a quarantine, commodity and structural fumigant is under scrutiny because its release to the atmosphere contributes to depletion of stratospheric ozone and it poses a risk to human health.

Approximately 35% of the methyl bromide (MeBr) sold in the United States is used for fumigating structures for pest control or for disinfesting commodities and harvested crops prior to shipment or sale (see e.g., Kurylo, M. J. et al. (1999), Short-lived ozone-related compounds, in Albritton G. M., Watson, R. T. and Auchamp, P. J. Eds. Scientific assessment of ozone depletion (1998), 2.1–2.37 Report No. 44, World Meteorological Organization, Geneva). In these uses, high levels of MeBr, generally between 17 g/m$^3$ to 42 g/m$^3$, are directly vented to the atmosphere following exposure to structures or commodities in closed containers. MeBr has a residence time of greater than 8 months in the troposphere allowing a significant fraction to be transported to the stratosphere where MeBr facilitates the destruction of ozone. The major use of MeBr, pre-plant field fumigation being 65% of sales, is currently being phased out by international agreement, particularly through the Montreal Protocol, as amended, and as a consequence of the 2001 United States Clean Air Act. Another methyl halide, MeI, is highly toxic to humans.

Several strategies have been proposed for capturing MeBr from the waste stream of commodity and structural fumigations followed by subsequent recycling or destruction, such as adsorption of MeBr on zeolite or on activated charcoal. Although approximately 80% of the treated MeBr may be recovered using a single bed or cartridge of activated charcoal adsorber, emissions of as high as 200 to 500 ppm MeBr (0.9 to 2.1 g/m$^3$) may result from this practice.

SUMMARY OF THE INVENTION

The present invention includes a process for oxidizing methyl halide contaminants comprising the steps of forming a reaction chamber containing a methylotrophic bacterium and contacting the methyl halide contaminants with such methylotrophic bacterium effective to cause direct oxidation of the methyl halide contaminant.

The present invention also includes a methylotrophic bacterium reaction chamber utilizing the process of directly oxidizing methyl halide contamrinants.

Furthermore, the present invention includes a process for oxidizing methyl bromide or methyl iodide used as a disinfectant comprising the steps of disinfecting one or more objects with the methyl bromide or methyl iodide, forming a reaction chamber containing a methylotrophic bacterium and contacting the methyl bromide or methyl iodide disinfectant, now contaminants, with the methylotrophic bacterium to cause direct oxidation of the methyl bromide or methyl iodide.

Additionally, the present invention includes a decontaminated object product produced by the process of oxidizing methyl bromide or methyl iodide used as a disinfectant.

Furthermore, the present invention includes a bioreactor containing a methylotrophic bacterium.

DETAILED DESCRIPTION OF THE PREFERRED EMBODIMENT

The present invention provides a process for oxidizing methyl halide contaminants, particularly MeBr and MeI, by forming a reaction chamber containing a methylotrophic bacterium and contacting the methyl halide contaminants with the methylotrophic bacterium in a manner to cause direct oxidation of the methyl halide contaminant.

Direct oxidation of methyl halide is shown as:

$$CH_3X + 1.5\ O_2 \rightarrow CO_2 + HX + H_2O,$$

with X representing a halide. For example, direct oxidation of methyl bromide proceeds by the following reaction:

$$CH_3Br + 1.5\ O_2 \rightarrow CO_2 + HBr + H_2O,$$

and direct oxidation of methyl iodide proceeds by the following reaction:

$$CH_3I + 1.5\ O_2 \rightarrow CO_2 + HI + H_2O$$

Figure 1:
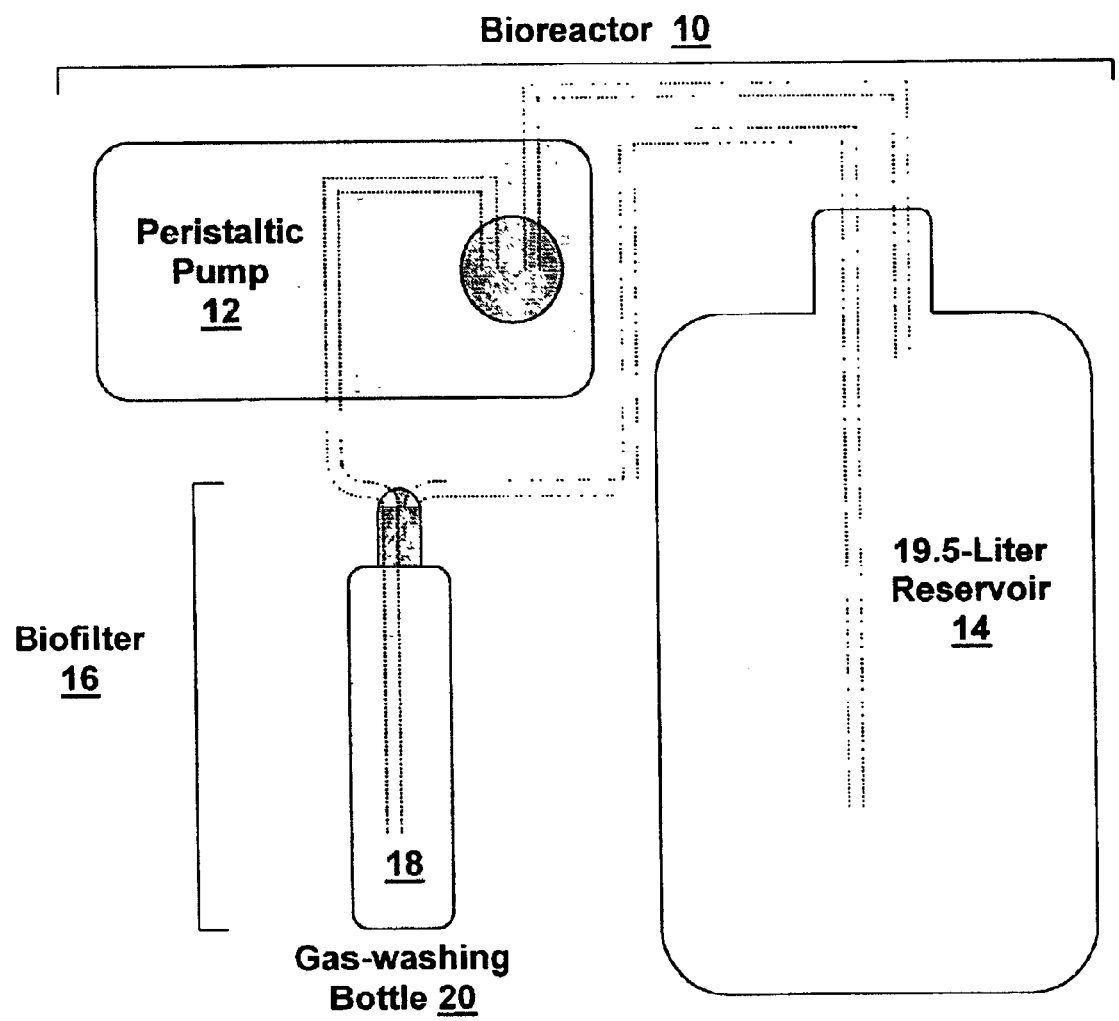
FIG. 1 is a schematic diagram of a bioreactor showing a peristaltic pump, reservoir and biofilter containing washed cells of strain IMB-1.

FIG. 1 shows a schematic diagram of a bioreactor 10 with a peristaltic pump 12, large reservoir 14 containing a methyl halide 30 contaminant and biofilter 16 containing washed cells of a methylotrophic bacterium 18. As seen in FIG. 1, the bioreactor 10 has a reaction chamber 20 (gas-washing bottle) where the biofilter 16 and methylotrophic bacterial 18 are protected. The methylotrophic bacterium 18 is formed in the reaction chamber 20 by placing a seed amount (inoculum) of the methylotrophic bacterium 18 therein for generation. The methylotrophic bacterium 18 comprises an organism that causes direct oxidation of the methyl halide 30 contaminant. Methylotrophic bacterium 18 includes those aerobic microorganisms that obtain energy and carbon for growth by oxidizing methyl substituent gas, other than methane. Methyl halides 30 are directly oxidized to $CO_2$ generally with a considerable amount of energy consumed by the microorganism for cell growth.

The methyl halide provides the microorganism with energy and carbon. Generally, no co-substrates need to be used with the microorganism 18 within the bioreactor 10, but may be used as an initial growth medium or regulator. Oxidation rates per cell remain constant, therefore as the cells grow, the process becomes more efficient. For example, an increase in the oxidation rate from about 9.5 to about 76 mg/h during the first 4 days of operation of the bioreactor was noticed in one experiment, during which time cell density increased from $3 \times 10_8$ cells/$cm^3$ to $2 \times 10^9$ cells/$cm^3$. Preferably the methylotrophic bacterium 18 comprises a Proteobacteria, such as for example, Strain MB2 (*Leisingeria methylhalidovorans*) having the recordation number of ATCC BAA-92, more preferably a 16S ribosomal RNA gene sequence in the Alpha subgroup of Proteobacteria, such as for example, CC495, and most preferably a 16S ribosomal RNA gene sequence in the Alpha subgroup of Proteobacteria designated strain IMB-1 having the accession number ATCC 202197. IMB-1 has been described in U.S. Pat. No. 6,013,254 to Oremland et al, entitled "Method for Enhancing Oxidation of Methyl Bromide with Strain IMB-1 (ATCC 202197) during Agricultural Fumigations," the disclosure of which is herein incorporated by reference. The complete sequence of the 16S rRNA gene from IMB-1 has been deposited in the GenBank database under accession no. AF034798.

Methylotrophic strain IMB-1 grows on several substrates including methyl bromide, methyl chloride, methyl iodide, methylated amines such as trimethylamine, glucose, pyruvate and acetate. When grown on glucose, for example, the enzyme required to oxidize high levels of methyl bromide must be induced by exposure to the compound. When strain IMB-1 is grown on methyl halides, the enzyme is constitutive. Phylogenetic analysis of the 16S ribosomal RNA gene sequence of strain IMB-1 indicates that the strain is classifiable in the Alpha subgroup of the Proteobacteria. This strain has the ability to directly oxidize MeBr or MeI and this ability is constitutive in cells regardless of the growth substrate.

Considering the morphology and phylogeny of strain IMB-1, strain IMB-1 is a motile, gram-negative rod having dimensions of approximately 1.3×0.6 μm. A phylogenetic tree generated from comparisons of the 16S ribosomal RNA gene sequences classifies strain IMB-1 in the Alpha subgroup of the Proteobacteria, as stated above. Strain IMB-1 is not closely related to recognized strains of methanotrophs or of methanol-utilizers but rather is more related to soil nitrogen-fixing bacteria of the genus Rhizobium. It is most closely related to strain ER2, a methylotroph which degrades methylcarbamate insecticides.

Strain IMB-1 has been shown to grow using MeBr as a sole source of carbon and energy. Growth was also obtained when methyl iodide served as the electron donor, and iodide accumulated in the medium as a consequence of this growth.

Strain IMB-1 also grows with glucose or acetate as electron donors. One-carbon compounds which support growth include mono-, di- and trimethylamine, but no growth occurred with methanol or formate. Pyruvate supported growth, but no growth occurred on succinate, fumarate or citrate, while weak growth was obtained on malate. Growth was obtained on methyl chloride, but no growth occurred on methyl fluoride or methane. Methyl fluoride (2–22 μmol/tube added) did not affect uptake of MeBr or growth of IMB-1 on MeBr. Growth on glucose, acetate, and methylamines was much more rapid than on the methyl halides, and also achieved higher cell densities. Strain IMB-1 was grown with the provision of ammonium salts in the medium. Table 1, below, shows growth on methyl halides.

TABLE 1

| SUBSTRATE (mmoles/L) | μ (specific growth rate) ($H^{-1}$) | $Y_M$ (growth yield) (g $mol^{-1}$) | MeBr oxidized (pmol/$10^6$ cells/h) |
|---|---|---|---|
| methyl bromide (0.8) | 0.03 | 4.2 | 1.4 |
| methyl chloride (0.8) | 0.03 | 3.4 | 1.7 |
| methyl iodide (0.3) | 0.07 | 2.7 | 2.4 |
| methyl fluoride (0.4) | 0.00 | 0.0 | 0.0 |

Procedures for forming the methylotrophic bacterium 18 within the bioreactor 10 include, for example and without limitation, strain IMB-1 being grown aerobically in batch mode using pulsed additions of MeBr for use as an inoculum for the bioreactor. Additions of MeBr from about 0.01 to about 0.1 g were made approximately daily for several weeks. Cells (1 L) were grown to elevated density (approximately $1.5 \times 10^8$ cells/$cm^3$) in stoppered, 2-L flasks with rotary shaking. Growth occurred in mineral salts media containing mono- and dibasic phosphate ($\Sigma PO_4^{3-} = 1.4$ mM) as well as sulfate and trace minerals (see e.g. Schaefer, J. K. and R. S. Oremland, Oxidation of Methyl Halides by the Facultative Methylotroph Strain IMB-1. Appl. Environ. Microbiol. 65 (1999): pp 5035–5041) the disclosure of which is hereby incorporated by reference. Media concentrations were tripled in order to provide additional nutrients and buffer capacity. Cells were grown at about 28° C. Cells were washed and re-suspended to 0.5 L in fresh media and transferred to the gas-washing bottle of the bioreactor having an initial cell density approximately equal to $3 \times 10^8$ cells/$cm^3$. Once the methylotrophic bacterium 18 constitutes part of the biofilter 16, the methyl halide is pumped from the reservoir 14 to the biofilter 16 for direct oxidation.

Cell suspensions readily oxidized $^{14}C$-MeBr to $^{14}CO_2$ after two consecutive transfers in medium in which the growth substrate was not a methyl halide. Thus, the ability of strain IMB-1 to oxidize MeBr was present regardless of the substrate that was utilized for growth. However, MeBr oxidation rates in methyl halide-grown cells were significantly higher than in cells grown on methylated amines, glucose or acetate (see e.g. FIG. 9 for comparison of MeBr uptake by glucose- vs. MeBr-grown cells at high cell density). The addition of methyl iodide to cells grown on methylamine initially retarded growth, resulting in a lag during which time methyl iodide was consumed. Cell suspensions harvested from these treatments had equivalent capacity to oxidize $^{14}$C-MeBr regardless of whether they were exposed to methyl iodide. When normalized for cell densities, the rate of MeBr oxidation (pmol/$10^6$ cells/h) was: 1.2, 1.4, 1.1, 1.1, and 1.4 for cultures incubated with 0, 2, 5, 8 and 10 μmoles MeI, respectively. Similar results were obtained when acetate or glucose were used as the electron donor instead of methyl amine.

Although methyl bromide can be oxidized by methane-oxidizing bacteria as well as by ammonia-oxidizing nitrifiers via the monooxygenases of the organisms, neither methanotrophs nor nitrifiers can use MeBr as a substrate to support growth. Thus, the ability of strain IMB-1 to achieve growth on McBr or MeI is unique. Methyl fluoride is not metabolized by strain IMB-1(see Table 1, above).

The ability of cells to oxidize MeBr was constitutive in strain IMB-1, regardless of whether it was grown on methyl halides or on glucose, acetate, or methylamines. When normalized for cell densities, cells grown on methyl halides had higher MeBr oxidation activity than those which were grown on other substrates. Cells grown on conventional substrates in the presence of trace levels of methyl iodide did not induce higher MeBr oxidation activity in cell suspensions. Although cells were able to oxidize the methyl iodide, they did not achieve any greater capacity to oxidize MeBr after they were grown out on methylamine, glucose, or acetate.

One method of cultivating the strain IMB-1is to use the mineral salts medium of Doronina et al. (see e.g. Doronina, N. V., A. P. Sokolov, and Y. A. Trotsenko, Isolation and Initial Characterization of Aerobic Chloromethane-utilizing Bacteria. FEMS Microbial. Lett. 142 (1996): pp. 179–183) as discussed in Connell Hancock, T. L., A. M Costello, M. E. Lidstrom, and R. S. Oremland, Strain IMB-1, A Novel Bacterium for the Removal of Methyl Bromide in Fumigated Agricultural Soils. Appi. Environ. Microbiol. 64 (1998): pp. 2899–2905), the disclosure of these references are hereby incorporated by reference. In this method, cells were grown in crimp-seal "Balch" tubes filled with 10 ml of medium and sealed with a 15 ml air headspace. Substrates were added by syringe injection and those tested for growth included methyl bromide, methyl iodide, methyl chloride, methyl fluoride, methane, Na formate, methanol, monomethylamine, dimethylamine, trimethylamine, Na acetate, glucose, sodium pyruvate, sodium citrate, sodium malate, and succinic acid. The pH was adjusted to 7.2, and after autoclaving, tubes were incubated at 30° C. with constant reciprocal shaking. Molar growth yield (Ym) values were obtained by dividing the amount of substrate consumed into the final cell density achieved, assuming that the cell dry weight was $3.4 \times 10^{-11}$mg/cell for the IMB-1isolate.

A MeBr oxidation assay was conducted on washed cell suspensions after cells were taken through two successive transfers on the substrate indicated. Ten ml of cells from the growth tubes were centrifuged (10,000 xg for 15 min. at 7° C.) and washed twice with mineral salts medium. The final pellets were resuspended in 5 ml of mineral salts medium, placed in 13 ml serum bottles and sealed with crimped butyl rubber stoppers. $^{14}$C-MeBr (1.0–2.0 μCi/bottle having a specific activity of 29.7 mCi/mmole and a purity of 100%, manufactured by New England Nuclear of Boston, Massachusetts) was injected and cells were incubated statically for four to six hours, at which time 0.25 ml 6 N HCl was injected to stop the reaction and liberate $^{14}$CO$_2$ into the gas phase. Tubes were vigorously hand shaken for 5 minutes before the gas phase was sampled for analysis.

In another series of experiments, varying trace levels of methyl iodide (MeI) were added to cells growing on glucose, methylamine, or acetate in determining that, as discussed above, pre-exposure to MeI increases the ability of harvested cell suspensions to oxidize $^{14}$C-MeBr.

Further to the discussion of FIG. 1, FIG. 1 shows a re-circulating bioreactor 10 employing a 19.5-liter glass carboy as a reservoir 14 with a 0.6-liter gas-washing bottle containing 0.5-liter washed cell suspension of IMB-1 as the biofilter 16. The biofilter 16 includes a mass of methylotrophic bacteria 18 within a container for bio-degradation of the methyl halides 30. The biofilter 16 constitutes the active surface of the bioreactor 10. The initial cell density was $3 \times 10^8$ cells/cm$^3$. The peristaltic pump 12 was used to circulate the methyl halide 30 gas in this system at a flow rate of 0.2 liter/min through inert rubber tubing (Pharmed), manufactured by Cole Parmer of Vernon Hills, Ill., and having 0.4 cm I.D. Stainless steel tubing (0.4 cm I.D.) was used to connect the components of the bioreactor 10. Methane (CH$_4$) was added (3.2 g/m$^3$) to serve as a control and an internal standard.

Figure 2:
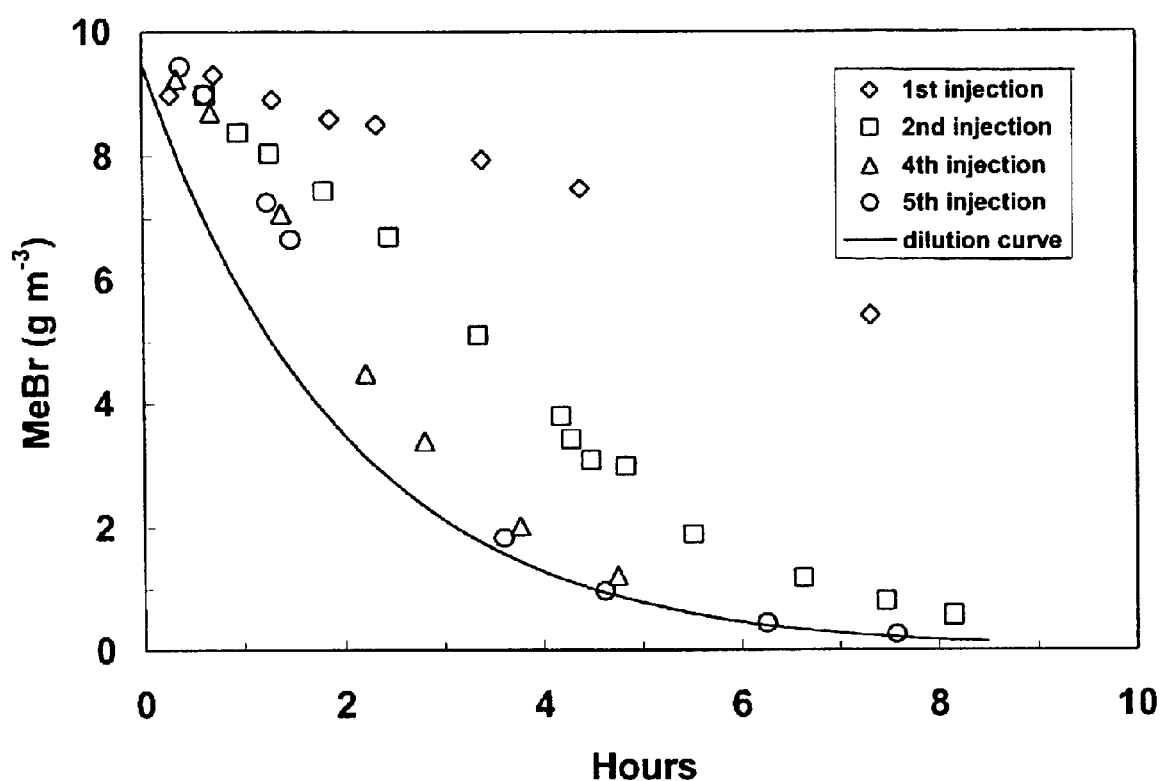
FIG. 2 is a graph showing oxidation of sequential additions of MeBr to strain IMB-1 in the bioreactor, with MeBr concentrations measured entering the gas-washing bottle following the first addition (◇), second addition (□), fourth addition (Δ), and fifth addition (○) of 0.21g and the solid line showing the dilution curve, calculated from the flushing time and the system volume, and represents the theoretical maximum uptake rate of MeBr.

FIG. 2 is a graph showing methyl bromide being removed faster following successive additions of 9 g/m$^3$ MeBr to growing cells over a four-day period. FIG. 2 shows oxidation of sequential additions of methyl bromide to strain IMB-1 in a bioreactor with (◇) representing the first addition, (□) representing the second addition, (Δ) representing the fourth addition, and (○) representing the fifth addition of 0.21 g. As seen in FIG. 2, and also in batch culture conditions, methyl bromide oxidation activity was initially slow with complete removal of 9 g/m$^3$ MeBr occurring within 12 to 24 hours. With subsequent additions of methyl bromide, oxidation occurred more rapidly such that after several equivalent additions all of the added MeBr was removed in approximately 6 hours.

Figure 3:
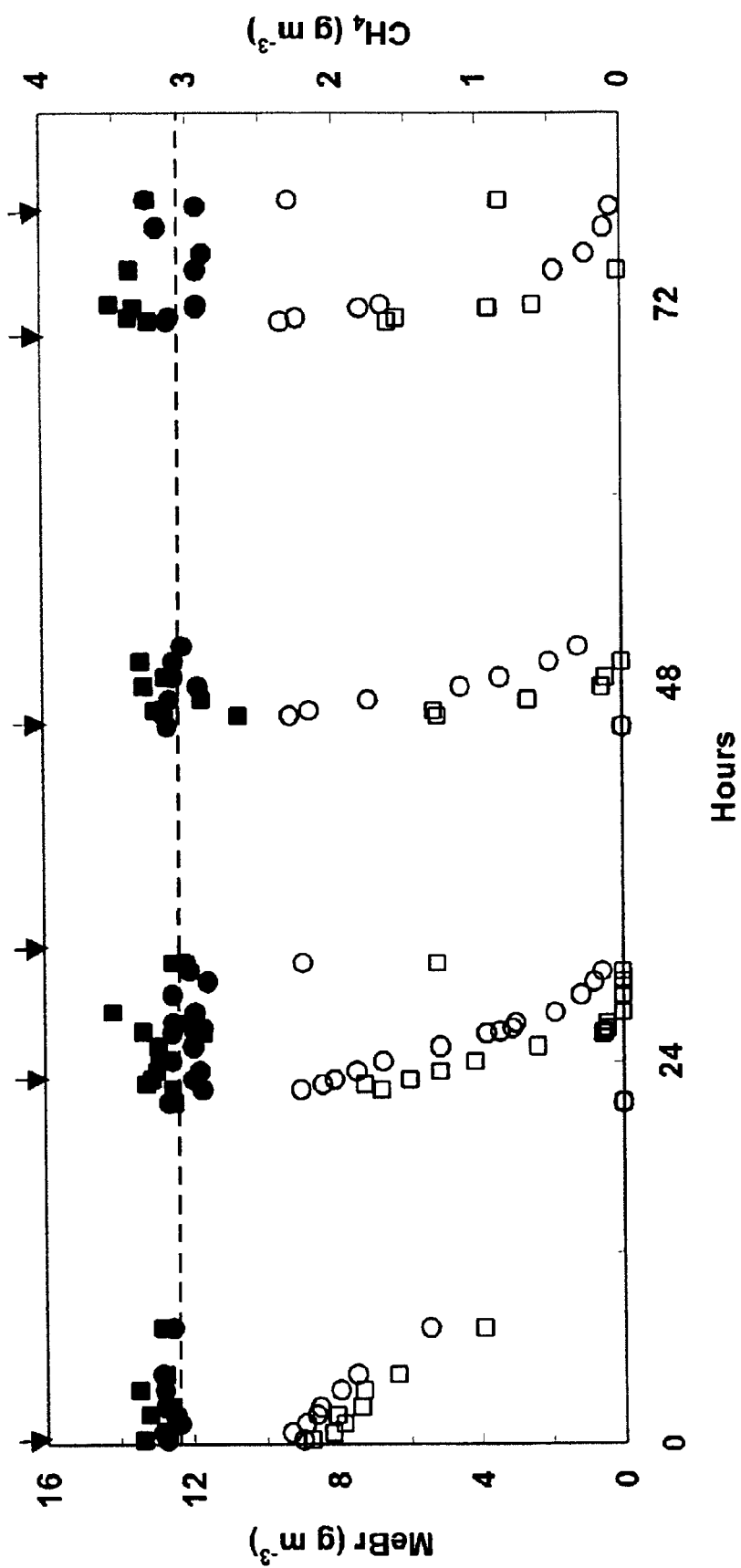
FIG. 3 is a graph showing repeated additions of MeBr to a bioreactor with uptake occurring over the first 80 hours of operation, having successive additions of added MeBr oxidized more rapidly than the first addition, with MeBr and methane ($CH_4$) concentrations in air entering the gas-washing bottle (circles) and exiting the gas-washing bottle (squares) shown and arrows indicating the time of addition of MeBr.

FIG. 3 is a graph showing repeated additions of methyl bromide to a bioreactor over 4 days, having successive additions of similar levels of added methyl bromide oxidized more rapidly and methyl bromide concentrations at any time being lower exiting the biofilter than in the carboy. FIG. 3 shows the methyl bromide (solid symbols) and CH$_4$ (open symbols) in air entering a cell suspension (circles) and exiting the cell suspension (squares). Initial levels of methyl bromide of 9 g/m$^3$ were oxidized by washed cell suspensions of strain IMB-1 within 24 hours. Repeated injections of slightly higher amounts of methyl bromide were oxidized more rapidly such that, after several additions, about 10 g/m$^3$ methyl bromide was removed in several hours, shown in FIG. 3.

Figure 4:
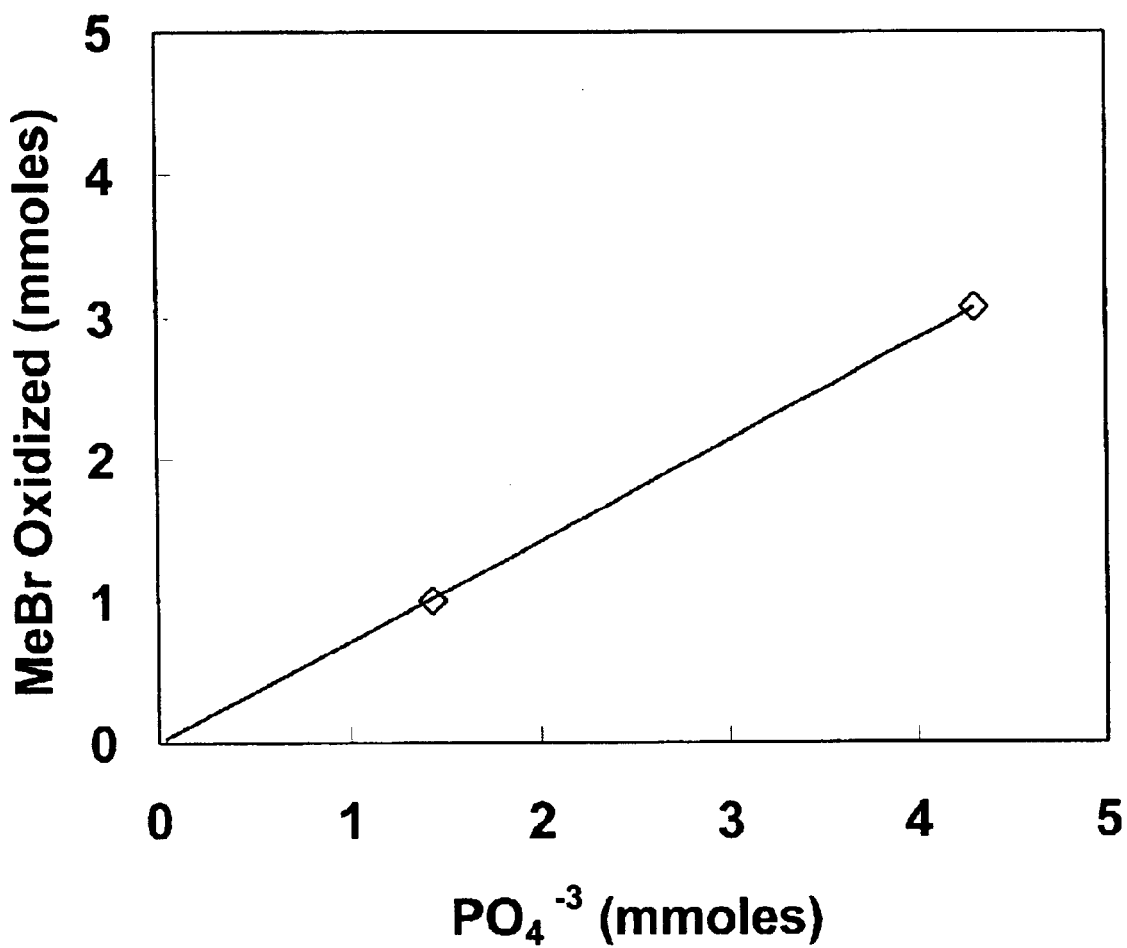
FIG. 4 shows the amount of MeBr oxidized by washed cell suspensions of strain IMB-1 in a bioreactor with the cells re-suspended in 1× and 3× strength phosphate media.

In buffered mineral salts medium, for example without limitation 0.012 M phosphate at pH=7.3 (see e.g., Doronina, et al.), the reaction continues until the available buffer capacity is exceeded and the pH decreases below 5, at which point the cells die. Additional buffering capacity was attained using growth media containing 0.039 M phosphate. FIG. 4 shows the amount of methyl bromide oxidized by washed cell suspensions of strain IMB-1 in a biofilter with the cells re-suspended in 1× and 3× strength phosphate buffer. As seen in FIG. 4, three times as much methyl bromide was degraded using the high phosphate buffer. As the scale of the reactor is increased, further buffering may be attained by continuously adjusting the pH of the media using sodium hydroxide (NaOH in a pH stat) or, if increased salinity becomes a problem, using slightly soluble solid carbonate materials, e.g., crushed clam shells or other like material. Triple strength phosphate buffer was used in all later experiments to re-suspend washed cells of strain IMB-1 in the biofilter.

Figure 5:
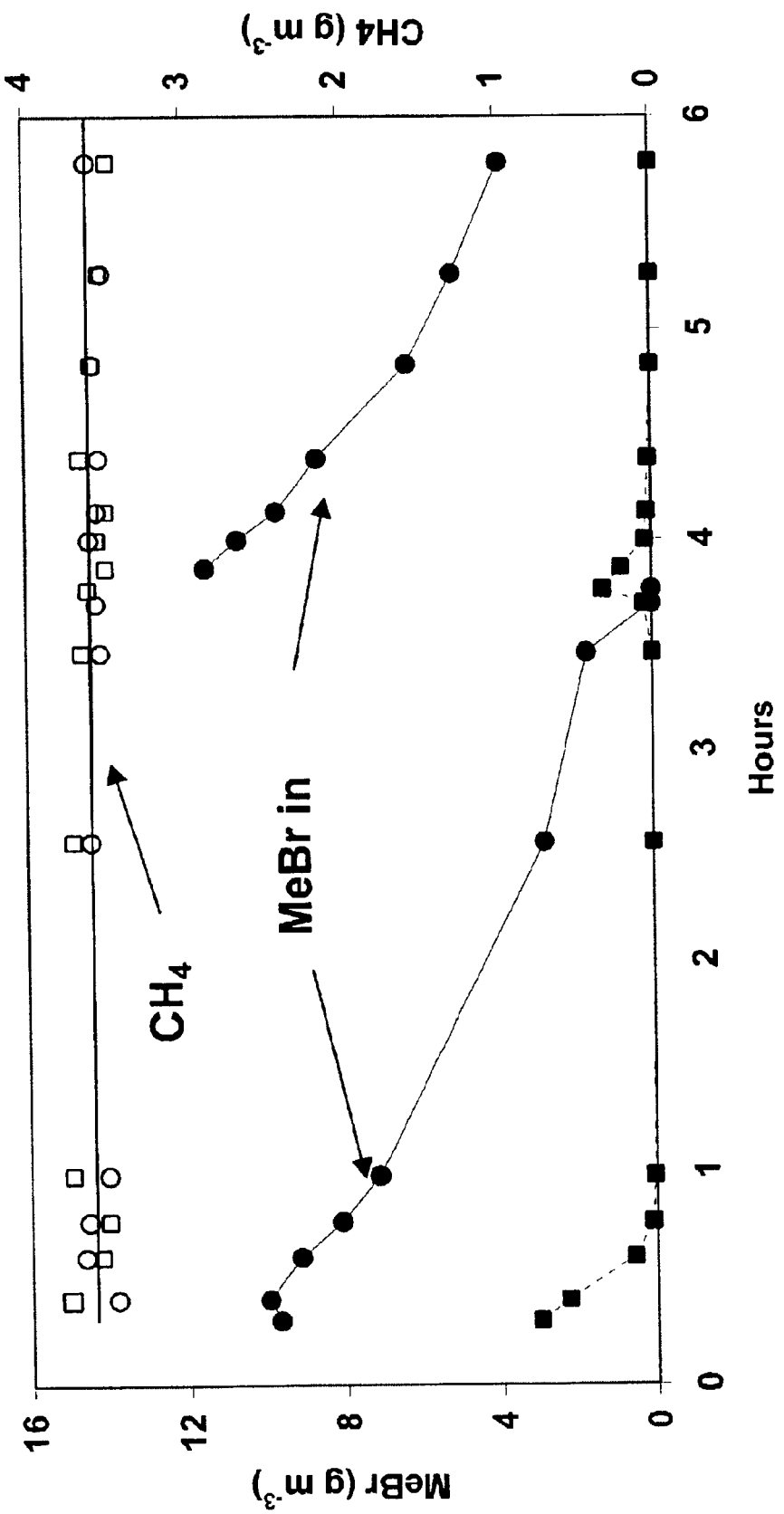
FIG. 5 shows MeBr oxidation by a washed cell suspension of strain IMB-1 in a bioreactor after 2 weeks operation showing faster uptake following the second of two additions of MeBr, with lower concentrations of MeBr in air exiting the gas-washing bottle than in air entering the gas-washing bottle shown using constant concentrations of $CH_4$ to indicate that there was no gas loss due to leaks.

FIG. 5 demonstrates MeBr oxidation by a washed cell suspension of strain IMB-1 in a bioreactor after 2 weeks operation showing faster uptake following the second of two additions of MeBr. Simultaneous measurements of the methyl bromide-in the carboy, i.e., entering the biofilter, and in the gas exiting the biofilter show that methyl bromide concentrations were reduced by up to 5 $g/m^3$ during a single pass through the filter. The constant concentrations of $CH_4$ indicate that there was no gas loss due to leaks.

The bioreactor may be designed to maximize the rate of oxidation of methyl bromide, particularly when using strain IMB-1. For example, without limitation, a twelve (12)-liter fermenter may be used to grow 10-L of cells of IMB-1 in batch culture for flow-through. Preferably, the fermenter is used in continuous-flow mode to grow IMB-1 using 21.2 $g/m^3$ MeBr as the feedstock. Use of strain 1 IMB-1 in a bioreactor is used in the present invention to directly oxidize various concentrations of the methyl halide, preferably methyl bromide or methyl iodide, for example without limitation high concentrations of approximately 30,000 ppm or 125 $g/m^3$. Direct oxidation of methyl bromide is most preferred.

Methyl halides may become contaminants through use thereof for fumigations and the like. Contaminated air containing these methyl halides occurs from practical uses of the methyl halides, such as fumigations using methyl bromide, sterilizations using methyl iodide, and the like. The contaminants are readily susceptible to bacterial biodegradation by aerobic bacterial processes. The present invention uses direct oxidation, preferably using microorganisms such as strain IMB-1. When placed into the bioreactor, the bioreactor employs bacterially mediated reactions to remove the methyl halide contaminants from large quantities of water or air effluent. Advantages of bioreactor include high efficiency and low cost of operation.

The methylotrophic bacterium reaction chamber of the process includes the microorganism and suitable structural support, such as the biofilter, for the microorganism to function, such as for example liquid, fluidized-bed, biotrickling and vapor-phase bioreactors. Preferably the methylotrophic bacterium reaction chamber includes a stirred-tank bioreactor, self-suspension bioreactor, fixed-film bioreactor or trickling bioreactor. The stirred-tank bioreactor includes suspended-growth reactors and has a suspension of cells in liquid medium through which the contaminant is continuously passed for treatment. A paddle or stirrer is used to mix the cell suspension. Gas exchange is by enhanced diffusion, e.g. using gas dispersion tubes, perforated tubes or bubblers.

The self-suspension bioreactor includes the characteristics of stirred-tank and suspended-growth bioreactors and utilizes the flow of the gas-phase or liquid-phase contaminants to provide physical mixing within the cell suspension. Gas exchange is by enhanced diffusion, e.g. using gas dispersion tubes, perforated tubes or bubblers.

The fixed-film bioreactor includes a physical support for the bacteria to grow on (examples include glass beads, soil, and perlite). A fixed-film bioreactor can be constructed in the following manner: A large cylinder constructed of inert materials (PVC plastic, stainless steel and/or glass) capable of containing 10 $m^3$ of solid, granular material, the surface of which is coated with attached bacteria derived from a cell suspension. A conveyance is needed to direct the contaminant methyl halides into the bioreactor. The cells are immobilized, usually by attaching to the surface of the support. This results in a stationary biofilm or layer of attached bacteria over which the contaminant is made to flow, either dissolved in liquid or in the gas phase.

The trickling bioreactor includes the fixed-film reactor with the addition of a flowing liquid phase to re-supply the biofilm with fresh bacteria or nutrients (or other required conditions) for continued growth. The trickling biofilter is constructed using a large cylinder of inert materials such as PVC plastic, stainless steel and/or glass which is capable of containing several 1 $m^3$ beds of solid, granular material (examples include glass beads, soil, and perlite). A re-circulating system, such as a pump and inert tubing, may be required to move liquid containing the bacterial cell suspension over the beds of solid granular material. The flowing liquid phase can also be used to remove waste products from the vicinity of the cells to allow continued growth. Degradation may be by the attached bacteria and by free (unattached) bacteria in the liquid.

Figure 6:
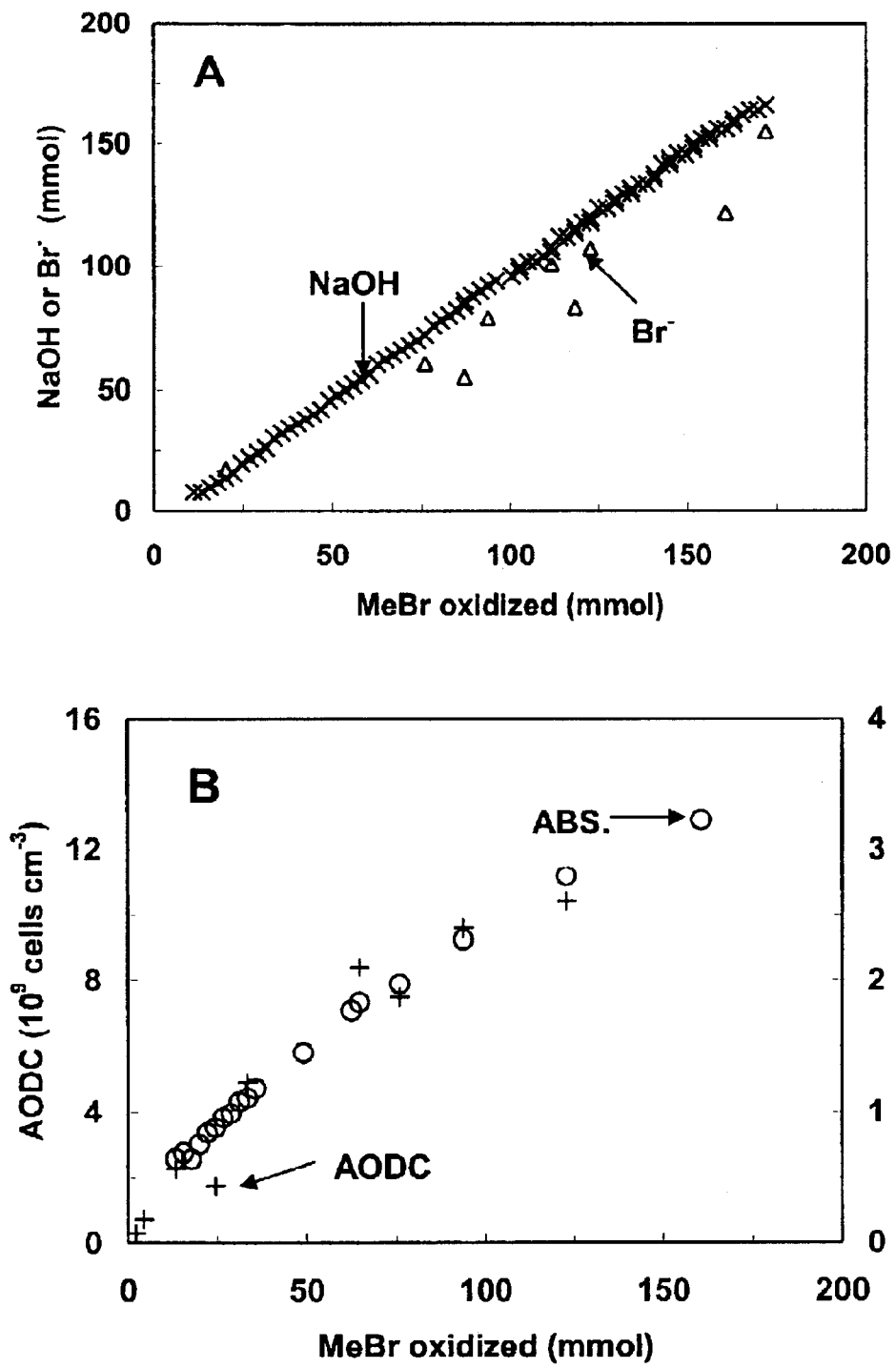
FIG. 6 is a graph showing the cumulative oxidation of McBr, added in pulses to the bioreactor over 45 days indicating (A) production of Br (Δ) and the cumulative amount of NaOH added (+) to maintain solution pH between 6.5 and 7.2 and (B) growth of strain IMB-1, indicated by acridine orange direct counts (AODC, +) and by solution absorbance measured at 680 nm (○)

FIG. 6A shows oxidation of methyl bromide added in pulses to a bioreactor over a forty-five day period, with the Δ representing production of $Br^{31}$, + representing the cumulative amount of NaOH added to maintain solution pH between 6.5 and 7.2. Bromide accumulated quantitatively in the spent medium as oxidation of MeBr proceeded. The increase in Br is shown to be directly proportional to the amount of MeBr oxidized. The amount of NaOH (mmoles) used to neutralize the strong acid (HBr) produced is equal to the amount of MeBr oxidized (mmoles) by strain IMB-1. The slope of the line representing the regression of MeBr oxidized vs. NaOH added is 1.0.

Growth of cells in the bioreactor may be represented by the graph shown in FIG. 6B, plotting cell production through oxidation of methyl halides by methylotrophic bacterium. FIG. 6B shows oxidation of methyl bromide added in pulses to a bioreactor over a forty-five day period, with the + representing growth of strain IMB-1, indicated by acridine orange direct counts (AODC), and the ○ representing solution absorbance measured at 680 nm. Preferably the graph represents either methyl bromide or methyl iodide. The graph shows growth of IMB-1 as acridine orange direct cell counts (AODC) and as optical density (absorbance) as a function of the amount of MeBr oxidized in the bioreactor. This graph demonstrates that the bacteria grow at the expense of the methyl halide since there is no other source of carbon or energy in the system. The growth phase is exponential. Growth is continuous and there is no lag in the production of cells upon exposure to the methyl halide.

Figure 7:
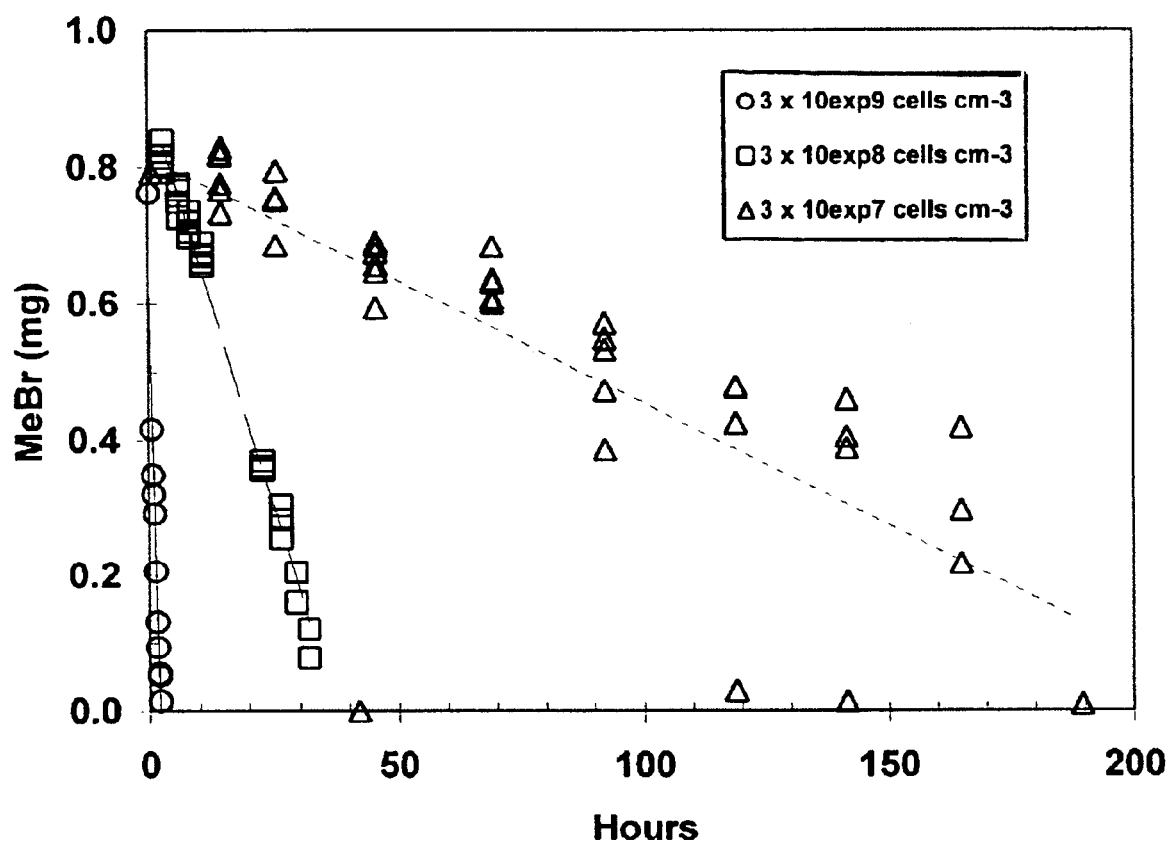
FIG. 7 is a graph showing oxidation of 0.76 mg added MeBr in bottles containing $3 \times 10^7$ cells/cm$^3$ (Δ), $3 \times 10^8$ cells/cm$^3$ (□), or $3 \times 10^9$ cells/cm$^3$ (○)

Care is exercised in introducing the methyl halide into the bioreactor because of health, e.g., toxicity, and incidental contamination concerns. Additionally in the case of MeBr, the toxicity of the MeBr compound to the organisms of the bioreactor can be controlled. FIG. 7 is a graph showing oxidation of 0.76 mg added methyl bromide in bottles containing $3\times10^7$ cells/$cm^3$ (Δ), $3\times10^8$ cells/$cm^3$ (□), or $3\times10^9$ cells/$cm^3$. Oxidation of MeBr increased with cell density during batch reactions using cell suspensions of strain IMB-1. Low levels of MeBr (0.76 mg, corresponding to 1.2 mM in the liquid) were removed within 8 days from bottles containing $1.5\times10^8$ cells and within 35 hours or 2 hours from bottles containing 10 or 100-fold more cells, respectively (see FIG. 7). Elevated amounts of MeBr (1.36 and 5.30 mg, corresponding to 2.1 and 8.2 mM in the liquid, respectively) were consumed more slowly but always with the same relationship of increased rate with greater cell numbers (see Table 2, below). Oxidation of MeBr on a per cell basis was nearly constant over the range of cell densities. MeBr was removed very slowly via chemical reactions from bottles with no added cells.

TABLE 2

| Amount of MeBr Added (mg) | MeBr Oxidation Rate (mg/d) | MeBr Oxidation Rate per Cell ($\times 10^{10}$ mg/cell-d) | MeBr Oxidation Rate Constant (per d) | $CO_2$ Production Rate (mg/d) |
|---|---|---|---|---|
| 0 cells | | | | |
| 0.76 | 0.029 | NA | NA | 0 |
| 1.36 | 0.062 | NA | NA | 0 |
| 5.30 | 0.208 | NA | NA | 0 |
| $3 \times 10^7$ cells/cm$^3$ | | | | |
| 0 | — | — | — | 0.003* |
| 0.76 | 0.063 | 4.1 | 0.083 | 0.031 |
| 1.36 | 0 | 0 | 0 | 0.002 |
| 5.30 | 0 | 0 | 0 | 0 |
| $3 \times 10^8$ cells/cm$^3$ | | | | |
| 0 | — | — | — | 0.011* |
| 0.76 | 0.555 | 3.7 | 0.73 | 0.224 |
| 1.36 | 0.180 | 1.2 | 0.13 | 0.189 |
| 5.30 | 0 | 0 | 0 | 0 |
| $3 \times 10^9$ cells/cm$^3$ | | | | |
| 0 | — | — | — | 0.363* |
| 0.76 | 6.53 | 4.4 | 8.6 | 5.025 |
| 1.36 | 3.52 | 2.3 | 2.59 | 1.990 |
| 5.30 | 6.07 | 4.0 | 1.14 | 2.696 |

*Rate of production of $CO_2$ in samples without added MeBr was used to correct all other rates for the effects of respiration.

Figure 8:
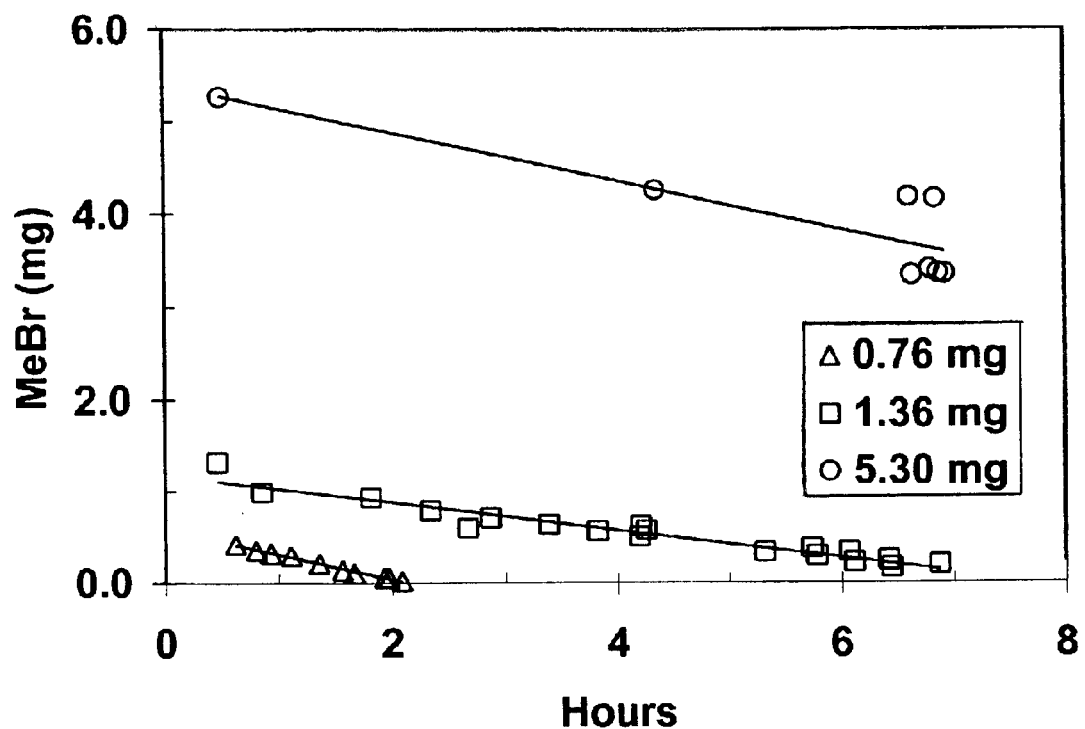
FIG. 8 is a graph showing oxidation of 0.76 mg (Δ), 1.36 mg (□), or 5.30 mg (○) MeBr in bottles containing $3 \times 10^9$ cells cm$^{-3}$ of strain IMB-1.

Oxidation of MeBr correlated inversely with the amount of substrate initially present. FIG. 8 is a graph showing oxidation of 0.76 mg (Δ), 1.36 mg (□), or 5.30 mg (○) MeBr in bottles containing 3×10$^9$ cells/cm$^3$ of strain IMB-1. In experiments with bottles containing 3×10$^9$ cells/cm$^3$, low levels of MeBr (0.76 mg) were removed within 2 hours, while moderate levels (1.36 mg MeBr) were removed within 7 hours. Initial rates of oxidation in bottles containing the highest levels (5.30 mg MeBr) were linear for the first 8 hours of the experiment, but subsequent degradation was by chemical means only (data not shown). Rates of oxidation of MeBr per cell were similar at all substrate concentrations (see Table 2), however rate constants decreased with increasing concentration suggesting that higher levels of added MeBr inhibited oxidation by bacteria.

Figure 9:
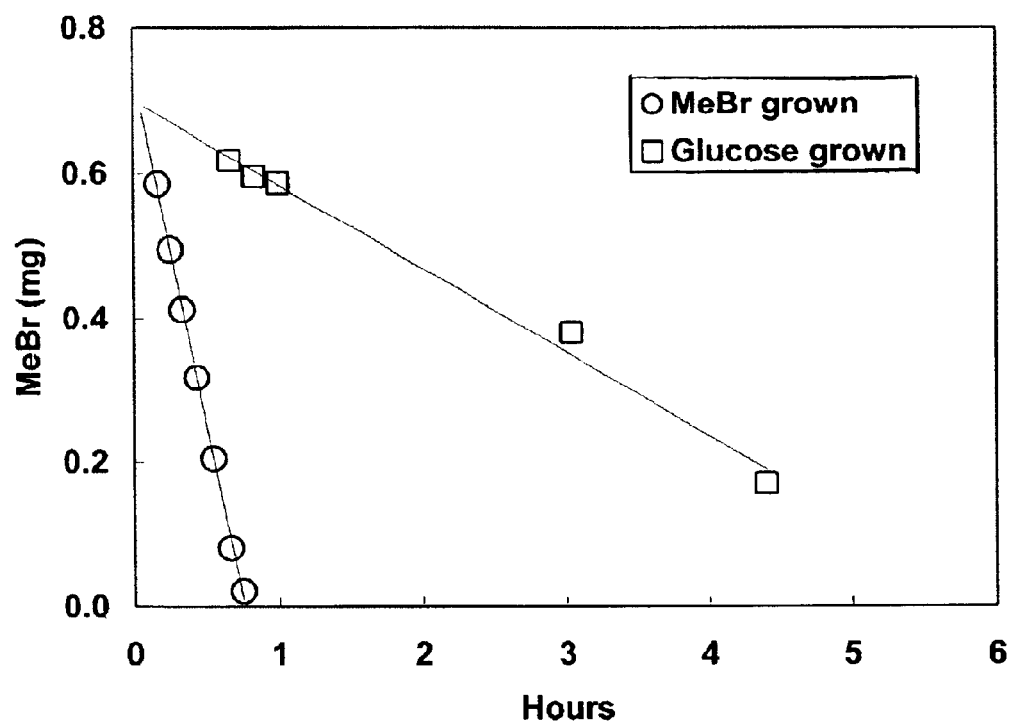
FIG. 9 is a graph showing oxidation of MeBr in bottles containing cells of strain IMB-1 grown on MeBr (○) or Glucose (□).

Production of $CO_2$ during the oxidation of MeBr was likewise inhibited by increased MeBr concentration. Initial rates of production of $CO_2$ were greatest in bottles with low levels of MeBr and decreased as MeBr increased (see Table 2, above). In bottles with low levels of added MeBr, rates of $CO_2$ production increased proportionally with cell density. At higher MeBr concentrations, only bottles containing the highest number of cells produced $CO_2$. No $CO_2$ was produced in bottles without added cells. FIG. 9 is a graph showing oxidation of methyl bromide in bottles containing cells of strain IMB-1 grown on MeBr (○) or glucose (□). Rates of oxidation of MeBr were greater in experiments with MeBr-grown cells than with cells grown on glucose (see FIG. 9). Low levels of MeBr corresponding to 1.2 mM in the liquid were oxidized within one hour during reaction with cells grown on MeBr whereas the reaction using glucose-grown cells required greater than 5 hours to remove a similar amount of MeBr. There were similar numbers of glucose-grown cells and MeBr-grown cells present (3.6×10$^8$ and 2.8×10$^8$ cells, respectively) however, MeBr grown cells removed MeBr seven-fold more efficiently on a per cell basis. Activation of the enzyme responsible for oxidation of MeBr was rapid, as no lag in MeBr uptake by the glucose-grown cells was observed.

A conveyor may be used to transport the methyl halide contaminant into the bioreactor. Conveyors include transport systems that collect the methyl halide from a contaminant location and inject the methyl halide into the bioreactor. Preferably the transport system is regulated to minimize spillage, leakage or other dispersions of the methyl halides during removal of the methyl halide from one location to the bioreactor. Additionally, it is preferred that the conveyor system minimizes the amount of dust, soil, and other debris, i.e., the conveyor system injects only the methyl halide into the bioreactor. Representative conveyors include a two-tarp apparatus for extraction of methyl halide from agricultural fields, transport of the extracted methyl halide from the agricultural fields and injection of the transported methyl halide into the bioreactor. The two-tarp apparatus includes a lower methyl halide permeable tarp and an upper methyl halide impermeable tarp. As the methyl halide diffuses from the soil and through the lower permeable tarp into the area between the two tarps, the methyl halide is collected for transport to the bioreactor. Collection may include the methyl bromide being swept into an activated charcoal adsorber or directly into the bioreactor. The two-tarp system for recovery of methyl bromide from agricultural field fumigations is further described in Chitwood, D. E. and Deshusses, M. A. Development of a Methyl Bromide Collection System for Fumigated Farmland, Environ. Sci. & Tech., 35: (2001) pp. 636–642, the disclosure of which is hereby incorporated by reference.

Charcoal trapping is suited to large volumes of contaminated air and can remove methyl bromide effectively at high flow rates, such as up to 20,000 liters/min. However, a single-pass, flow-through charcoal adsorber only removes 80% of the methyl bromide. Use of the bioreactor containing the methylotrophic bacterium after use of the single charcoal adsorber is preferred for effective lowering of methyl bromide emissions well below the initial 80%. Alternatively, the methyl halide may be thermally desorbed from the charcoal, either locally or at a distant site, using flowing air, which is then treated in the biofilter. Incremental introduction of the MeBr may be done by dampening the load of fumigant, for instance by adsorption onto a solid surface such as activated charcoal, followed by release and controlled introduction into the bioreactor.

The bioreactor of the present invention may provide 100% efficiency in removing the methyl halide added, e.g., 100% of the methyl bromide added is degraded. The capability occurs from the direct oxidation of methyl halide by the microorganism, providing increasing amount of microorganism over time for consumption of the methyl halide. Efficiency of removal of methyl halide on a per cell basis is constant during the operation of the bioreactor.

The present invention further includes a process for oxidizing methyl halides used as a disinfectant. After methyl bromide or methyl iodide is used for disinfecting one or more objects, the methyl bromide or methyl iodide becomes a contaminant. The contaminant methyl bromide or methyl iodide is added (e.g., injected) into a reaction chamber containing the methylotrophic bacterium, and with contact therein, is directly oxidized.

Methyl bromide and methyl iodide may be used to disinfect objects, such as without limitation, articles, buildings, structures, agricultural fields, ships, vehicles, ships and other sea-going vessels, mail, mail boxes, medical instruments, clothing, furniture, books and other such non-living items. Also, methyl halides, especially methyl bromide, are used to disinfect durable and perishable commodities, such as nuts, fruits, vegetables, and fresh and dried flowers. Disinfection includes the sterilization, fumigation, decontamination, disinfestation, and the like of a desired object. Hence without limitation, vermin such as rats, mice, and other rodents, infectious microorganisms such as *Bacillus anthracis* (anthrax) and its spores, other pathogenic bacteria, small pox, fungi and the like, insects such as locust, cockroaches, ticks, etc., and other like nuisance organisms are killed. Methyl bromide is known to kill B. anthracis (anthrax bacteria) and its spores (see e.g., Kolb, R. W. and Schneiter, R. 1950. Germicidal and sporicidal efficacy of methyl bromide for Bacillus anthracis. Ind. Hyg. Newsletter, U.S. Pub. Health Service, vol. 10), with methyl bromide functioning both as a microbicide and a pesticide at about the same levels (such as about 25,000 ppm as reported in Schade, J. E., and King, A. D. Jr. 1977. Methyl bromide as a microbicidal fumigant for tree nuts. Appl. and Environm. Microbiol., vol. 33, 1184–1191). In accordance with the present invention, methyl bromide may be used to fumigate one or more objects that are contaminated with spores of *B. anthracis*, with recovered MeBr gases processed as taught herein. The decontamination of the object (s) and removal of the methyl bromide therefrom yields a decontaminated object.

EXAMPLE 1A

Bioreactor for the Removal of Methyl Bromide Following Contained Fumigations A closed-system bioreactor was built using the general design of FIG. 1 and employed for testing on a laboratory bench. The bioreactor was started with 0.5 L of growing culture of methylotrophic bacteria strain IMB-1 and removed MeBr at fumigation concentrations (>17 g/$m^3$) from re-circulating air. Strain IMB-1 grew to high cell densities ($5\times10^9$ cells/$cm^3$) in the bioreactor within several days using pulsed additions of MeBr as the sole carbon and energy source. The addition of the MeBr was done as a gas. Bacterial oxidation of MeBr produced $CO_2$ and hydrobromic acid (HBr) which could be neutralized by addition of NaOH. Strain IMB-1 was capable of sustained oxidation of large amounts of MeBr (16 g in 46 days). Oxygen in the bioreactor decreased from 21% to below 5% (v/v) resulting in decreased oxidation activity, which was partially restored by adding oxygen. Oxidation of MeBr was unaffected by the presence of elevated dissolved solutes (>26 g/kg) that approached the salinity of seawater. Strain IMB-1 grown on MeBr was 7 times more efficient at removing MeBr from the headspace of flasks than cultures grown on glucose (55 vs. $8\times10^{-15}$ g MeBr/cell/hr, respectively). An open-system bioreactor having 10 L of growing culture used a continuous supply of MeBr (21.2 g/$m^3$ in air). Growth of strain IMB-1 was continuous and 80 g of MeBr was removed from the air supply in 15 days.

EXAMPLE 1B

Buffering pH in the Bioreactor

Oxidation of MeBr by growing cell suspensions of strain IMB-1 proceeded until the available substrate was utilized or until a pH limitation was reached. Cell death occurred when the solution pH dropped from 7.2 to below 5.0 and was determined by cessation of MeBr uptake and/or by observable foaming in the bioreactor. Increasing the buffer capacity of the phosphate media from single-strength (1×) to triple-strength (3×) resulted in a proportional increase in the amount of methyl bromide that could be oxidized (see FIG. 4).

Solution pH could be further controlled in growing cultures with the addition of NaOH as required. In a test of the capacity of the bioreactor, MeBr added in pulses of 0.21 g, up to three times a day for 46 days, resulted in the oxidation of 16.2 g of MeBr. Solution pH was maintained between 6.5 and 7.0 by the addition of 1 mole of NaOH for each mole of MeBr oxidized (see FIG. 6A). Cell growth, monitored as absorbance and direct counts, was continuous (see FIG. 6B).

EXAMPLE 1C

MeBr Oxidation-in the Bioreactor

Concentrations of $CH_4$ remained constant throughout the experiments (see FIG. 3 and FIG. 5). Concentrations of MeBr were much greater in the gas entering the cell suspension than in the gas exiting the cell suspension.

The first addition of 0.21 g MeBr was removed in 24 hours (see FIG. 2). The solid line is the dilution curve, calculated from the flushing time and the system volume, and represents the theoretical maximum uptake rate of MeBr. Subsequent additions were removed more rapidly, such that, by the third day of operation, 0.21 g added MeBr was consumed within 4 hours. Concentrations of $O_2$ decreased in the bioreactor from an initial (atmospheric) value of 21% to about 5% after 30 days operation. During this time, $CO_2$ in the gas increased from an initial (atmospheric) value of 0.04% to about 10%.

EXAMPLE 2A (prophetic)

Methyl bromide concentration is adsorbed using activated charcoal in a waste stream with eighty percent efficiency, reducing the MeBr concentration from 10,000 ppm to 500 ppm. The remaining MeBr is processed in the bioreactor of the present invention directly following the activated charcoal.

EXAMPLE 2B (prophetic)

The process of Example 2A was followed with the exception that the adsorbed MeBr is desorbed from the activated charcoal by electrothermal regeneration or by flowing hot air over the charcoal adsorber. The desorbed McBr is subsequently processed in the bioreactor of the present invention.

EXAMPLE 3 (prophetic)

A stirred tank bioreactor is constructed using a large stainless steel tank capable of containing 10 liters of cell suspension and employing a method of gas dispersion that insures rapid dissolution of the methyl halide contaminant such as gas dispersion tubes. A motor and stirrer operated at 50 RPM may be required to mix the suspension.

EXAMPLE 4 (prophetic)

A self-suspension bioreactor is constructed in the following manner: A large stainless steel tank capable of containing 100 liters of cell suspension is used with a method of gas dispersion that insures rapid dissolution of the methyl halide contaminant.

EXAMPLE 5 (prophetic)

A fixed-film bioreactor is constructed of a large stainless steel cylinder containing 10 $m^3$ of perlite, the surface of which is coated with attached bacteria derived from a cell suspension. Contaminant methyl halides are injected into the bioreactor using air blowers.

EXAMPLE 6 (prophetic)

A trickling bioreactor is constructed using a large stainless steel cylinder capable of containing several 1-m$^3$ beds of perlite and a re-circulating system with a pump and inert tubing to move liquid containing the bacterial cell suspension over the beds of perlite. Contaminant methyl halides are injected into the bioreactor using air blowers.

EXAMPLE 7a (prophetic)

Removal of Anthrax from a Building

Anthrax is introduced into a building through its ventilation system and people are evacuated. The building is fumigated with methyl bromide. Following a period of contact with the objects in the building, the MeBr (now a contaminant) is pumped out of the building to be replaced, at the end opposite the pump, with outside air. The contaminated air is pumped directly through a bioreactor.

EXAMPLE 7b (prophetic)

Removal of Anthrax from a Building

When the exiting MeBr concentration of Example 7a is greater than about 20,000 ppm the bioreactor is used following (in series with) a process to adsorb MeBr on activated charcoal or zeolite. The bioreactor may also be used to treat MeBr contaminated air arising from desorption of the methyl bromide from the activated charcoal or zeolite adsorber.

EXAMPLE 8a (prophetic)

Removal of Anthrax from Mail

Anthrax is placed in an envelope and mailed. The contaminated object (mail) is placed in a container for fumigation. The container is fumigated with methyl bromide. Following a period of contact with the object in the container, the MeBr (now a contaminant) is pumped out of the container to be replaced, at the end opposite the pump, with outside air. The contaminated air is pumped directly through a bioreactor.

EXAMPLE 8b (prophetic)

Removal of Anthrax from Mail

When the flow rate of MeBr exiting the container of example 8a is excessive then the bioreactor is used following (in series with) a process to adsorb MeBr on activated charcoal or zeolite. The bioreactor may also be used to treat MeBr contaminated air arising from desorption of the methyl bromide from the activated charcoal or zeolite adsorber.

The foregoing summary, description, and examples of the present invention are not intended to be limiting, but are only exemplary of the inventive features which are defined in the claims.

What is claimed is:

1. A process for oxidizing methyl halide contaminants, wherein the methyl halide contaminant is selected from the group of methyl bromide and methyl iodide, comprising the steps of:

forming a reaction chamber containing a methylotrophic bacterium; contacting the methyl halide contaminants with such methylotrophic bacterium effective to cause direct oxidation of the methyl halide contaminant, and controlling the pH of the direct oxidation reaction wherein a pH of at least about 5 is maintained.

2. The process of claim 1, wherein the methylotrophic bacterium comprises a Proteobacteria.

3. The process of claim 2, wherein the methylotrophic bacterium comprises a 16S ribosomal RNA gene sequence in the Alpha subgroup of Proteobacteria.

4. The process of claim 3, wherein the methylotrophic bacterium comprises a 16S ribosomal RNA gene sequence in the Alpha subgroup of Proteobacteria designated strain IMB-1 having the accession number ATCC 202197.

5. The process of claim 1, further comprising the step of adding a buffer medium to the reaction chamber.

6. The process of claim 5, wherein the methyl halide contaminant comprises methyl bromide.

7. The process of claim 5, wherein the methyl halide contaminant comprises methyl iodide.

8. A process for oxidizing methyl halide used as a disinfectant comprising the steps of:

disinfecting one or more objects with methyl halide, with the methyl halide becoming a contaminant thereafter;

forming a reaction chamber containing a methylotrophic bacterium;

contacting the methyl halide contaminants with such methylotrophic bacterium effective to cause direct oxidation of the methyl halide contaminant, wherein the methyl halide is selected from the group consisting of methyl bromide and methyl iodide; and, controlling the pH of the direct oxidation reaction wherein a pH of at least about 5 is maintained.

9. The process of claim 8, herein the methyl halide comprises methyl bromide.

10. The process of claim 8, wherein the one or more objects comprises possible anthrax contamination.

11. The process of claim 1, wherein the controlling step comprises the addition of NaOH, to the reaction chamber.

12. The process of claim 5, wherein the buffer medium comprises a phosphate buffer medium.

13. The process of claim 8, wherein the controlling step comprises the addition of NaOH to the reaction chamber.

14. The process of claim 13, further comprising the step of adding a buffer medium to the reaction chamber.

15. The process of claim 14, wherein the buffer medium comprises a phosphate buffer medium.

* * * * *